United States Patent
Cao et al.

(10) Patent No.: US 11,627,980 B2
(45) Date of Patent: Apr. 18, 2023

(54) ULTRASONIC SCALPEL BIT (71) Applicant: JIANGSU SMTP TECHNOLOGY CO., LTD., Jiangsu (CN)

(72) Inventors: Qun Cao, Beijing (CN); Songtao Zhan, Beijing (CN)

(73) Assignee: Jiangsu SMTP Technology Co., Ltd., Jiangsu (CN)

( * ) Notice: Subject to any disclaimer, the term of this patent is extended or adjusted under 35 U.S.C. 154(b) by 190 days.

(21) Appl. No.: 16/489,305

(22) PCT Filed: Feb. 9, 2018

(86) PCT No.: PCT/CN2018/075951
§ 371 (c)(1),
(2) Date: Aug. 27, 2019

(87) PCT Pub. No.: WO2018/161772
PCT Pub. Date: Sep. 13, 2018

(65) Prior Publication Data
US 2020/0029996 A1    Jan. 30, 2020

(30) Foreign Application Priority Data
Mar. 10, 2017   (CN) .......................... 201720232078.5

(51) Int. Cl.
*A61B 17/32* (2006.01)
*A61B 17/3211* (2006.01)

(52) U.S. Cl.
CPC .. *A61B 17/320068* (2013.01); *A61B 17/3211* (2013.01); *A61B 2017/320075* (2017.08)

(58) Field of Classification Search
CPC ............ A61B 17/3211; A61B 17/3213; A61B 17/320068; A61B 17/1671;
(Continued)

(56) References Cited

U.S. PATENT DOCUMENTS 5,047,043 A    9/1991  Kubota et al.
5,188,102 A *  2/1993  Idemoto .............. A61M 3/0279
                                             606/45
(Continued)

FOREIGN PATENT DOCUMENTS

CN    201070394 Y    6/2008
CN    102100574 A    6/2011
(Continued)

OTHER PUBLICATIONS

International Application No. PCT/CN2018/075951, International Search Report dated May 8, 2018, 2 pages.
(Continued)

*Primary Examiner* — Kathleen S Holwerda
*Assistant Examiner* — Lauren Dubose
(74) *Attorney, Agent, or Firm* — Kilpatrick Townsend & Stockton LLP (57) ABSTRACT

Disclosed is an ultrasonic scalpel bit, comprising a bit tip (1), a bit bar (2) and a bit body (3), one end of the bit bar (2) being connected to the bit tip (1), and the other end of the bit bar (2) being connected to the bit body (3), wherein a main body of the bit tip (1) is of a flat sheet structure, an upper and a lower face of which respectively form an upper bit ridge (11) and a lower bit ridge (12) of the bit tip (1); a protrusion (14) is formed at a front end of the upper bit ridge (11); the upper bit ridge (11) has a thickness greater than that of the flat sheet structure and that of the lower bit ridge (12); and the protrusion (14) is smooth and free of edges.

8 Claims, 6 Drawing Sheets

(58) Field of Classification Search
CPC ........... A61B 2017/32113; A61B 2017/32116;
A61B 2017/320074; A61B 2017/320075;
A61B 2017/320072; A61B 2090/08021;
A61B 17/3209; A61B 17/1657; A61B
2017/320082; A61B 90/03; A61B
2090/033; A61B 2090/035; A61B
2090/036; A61F 9/00745
USPC ........................................................... 30/357
See application file for complete search history.

(56) References Cited

U.S. PATENT DOCUMENTS

| | | | |
|---|---|---|---|
| 5,391,144 A | 2/1995 | Sakurai et al. | |
| 8,894,673 B2 | 11/2014 | Darian | |
| 2005/0177184 A1 | 8/2005 | Easley | |
| 2008/0058775 A1 | 3/2008 | Darian et al. | |
| 2009/0143795 A1* | 6/2009 | Robertson | A61B 17/3205 606/169 |
| 2013/0090660 A1* | 4/2013 | Darian | A61B 17/14 606/84 |
| 2013/0158585 A1* | 6/2013 | O'Brien | A61B 17/3209 606/172 |
| 2013/0204285 A1* | 8/2013 | Gouery | A61B 17/320068 606/169 |
| 2014/0058427 A1 | 2/2014 | Robertson | |
| 2017/0000513 A1 | 1/2017 | Conlon et al. | |
| 2017/0020552 A1 | 1/2017 | Yoshimine | |

FOREIGN PATENT DOCUMENTS

| | | |
|---|---|---|
| CN | 202146334 | 2/2012 |
| CN | 202920294 U | 5/2013 |
| CN | 103431894 | 12/2013 |
| CN | 205831876 U | 12/2016 |
| EP | 1 736 107 A1 | 12/2006 |
| JP | 047807 | 1/1992 |
| JP | 2014533132 | 12/2014 |
| KR | 20150095748 A | 8/2015 |
| KR | 20160000984 A | 1/2016 |

OTHER PUBLICATIONS

Application No. PCT/CN2018/075951, International Preliminary Report on Patentability, dated Sep. 19, 2019, 6 pages.

* cited by examiner

ULTRASONIC SCALPEL BIT

CROSS-REFERENCE TO RELATED APPLICATIONS

This application is a 371 National Stage of International Application No. PCT/CN2018/075951, filed Feb. 9, 2018, which claims priority to Chinese Application No. 201720232078.5 (CN), filed Mar. 10, 2017, both of which are hereby incorporated by reference in their entireties for all purposes.

TECHNICAL FIELD

The present disclosure belongs to the technical field of medical instruments, and in particular to an ultrasonic scalpel bit.

BACKGROUND ART

In modern society, with the development of medical technologies, orthopedic surgery shows a tendency of diversification. Accordingly, when performing surgery, it is necessary to use different shapes of scalpel bits for different orthopedic conditions to perform cutting, grinding, scraping, clamping and other operations on an affected area. In orthopedic surgery, ultrasonic scalpels are typically used to cut, grind, plane, scrape, or arbitrarily shape bones. Sheet-shaped bits of existing ultrasonic scalpels are bits which mainly have a cutting function. However, at present, such bits mostly have the shape of a straight sheet. When it is necessary to bypass a spinal cord to cut a posterior portion of a vertebral body during an osteotomy operation, a large operating space is required to allow such bits to enter the front of the spinal cord, which is extremely inconvenient for operation. Moreover, there is no protective measure on the bits at the front, which may easily cause injury to the spinal cord due to operational errors, resulting in medical accidents.

SUMMARY OF THE DISCLOSURE

In order to solve the existing technical problems mentioned above, the present disclosure proposes an ultrasonic scalpel bit, comprising a bit tip, a bit bar and a bit body, one end of the bit bar being connected to the bit tip, and the other end of the bit bar being connected to the bit body, wherein a main body of the bit tip is of a flat sheet structure, an upper and a lower face of which respectively form an upper bit ridge and a lower bit ridge of the bit tip; a protrusion is formed at a front end of the upper bit ridge; the upper bit ridge has a thickness greater than that of the flat sheet structure and that of the lower bit ridge; and the protrusion is smooth and free of edges.

In the ultrasonic scalpel bit of the present disclosure, preferably, the bit tip is bent to one side at a portion of the bit tip that is connected to the bit bar, such that the bit tip is at an angle to the bit bar.

In the ultrasonic scalpel bit of the present disclosure, preferably, the protrusion is in the shape of a circle or an ellipse.

In the ultrasonic scalpel bit of the present disclosure, preferably, the lower bit ridge is of a blade-like structure or a toothed structure.

In the ultrasonic scalpel bit of the present disclosure, preferably, a front end of the bit tip is provided with a front-end bit blade.

In the ultrasonic scalpel bit of the present disclosure, preferably, the upper bit ridge transitions to the lower bit ridge through a circular arc-shaped portion at a tip head of the bit tip, the arc-shaped portion being provided with a toothed structure.

In the ultrasonic scalpel bit of the present disclosure, preferably, the protrusion transitions to the front-end bit blade of the bit tip through a step, a circular arc or a bevel.

In the ultrasonic scalpel bit of the present disclosure, preferably, the bit bar is of a hollow structure, the hollow structure extending up to the front end of the bit tip, and a liquid injection hole is provided in a side face of a cylindrical structure of the bit tip, or a side face of a flat-sheet-shaped cutting portion of the bit tip, or the foremost end of the bit tip.

In the ultrasonic scalpel bit of the present disclosure, preferably, the bit bar is connected to the bit tip and the bit body respectively through a bevel or a circular arc-shaped face with a smooth transition.

In the ultrasonic scalpel bit of the present disclosure, preferably, the other end of the bit body is connected to a specific ultrasonic host via an ultrasonic transducer, and the other end of the bit body is provided with connection threads, which are internal or external connection threads.

The ultrasonic scalpel bit has the following beneficial effects:

(1) The ultrasonic scalpel bit of the present disclosure can concentrate all the energy generated by the ultrasonic transducer on the front end portion of the bit, so that the front end portion of the bit of the tool has the highest energy output, achieving the strongest working effect.

(2) The head-protected ultrasonic scalpel bit of the present disclosure can help a surgeon to bypass the spinal cord for performing a longitudinal cutting operation in a narrow space during a posterior osteotomy operation for vertebral body resection, and provides a safe protection part, so that it is possible to safely complete the operation without hurting the spinal cord. The time of surgery is shortened, and the safety of the operation is improved.

(3) The ultrasonic scalpel bit of the present disclosure is of a hollow structure, and the bit tip of the bit is provided with a liquid injection hole, which can ensure that the injected liquid flows out of the bit tip of the bit, and that excised tissues can be immediately discharged, the visual field at an incision is clear and clean, and the remaining tissues to be retained can be protected from being damaged. In this way, the risk of the surgery is further reduced, and the safety and success rate of surgery are improved.

IN THE FIGURES

1—Bit tip; 11—Upper bit ridge; 12—Lower bit ridge; 13—Front-end bit blade; 14—Protrusion; 2—Bit bar; 3—Bit body; 31—Connection threads; 32—Clamping face; 16—Tooth.

DETAILED DESCRIPTION OF EMBODIMENTS

The technical solution of the present disclosure will be clearly and completely described below in conjunction with the accompanying drawings, and obviously, the described embodiments are part of, not all of, the embodiments of the present disclosure. All other embodiments obtained by those of ordinary skill in the art based on the embodiments of the present disclosure without any creative effort shall fall within the scope of protection of the present disclosure.

In the description of the present disclosure, it should be noted that the orientation or position relations indicated by the terms "center", "upper", "lower", "left", "right", "vertical" "horizontal", "inner", "outer", etc. are based on the orientation or position relation shown in the accompanying drawings and are intended to facilitate the description of the present disclosure and simplify the description only, rather than indicating or implying that the device or element referred to must have a particular orientation or be constructed and operated in a particular orientation, and will not be interpreted as limiting the present disclosure. In addition, the terms "first", "second" and "third" are for descriptive purposes only and should not be construed as indicating or implying relative importance.

In the description of the present disclosure, it should be noted that the terms "mounting", "connecting" and "connection" should be understood in a broad sense. Unless otherwise explicitly specified or defined, for example, it may be a fixed connection, a detachable connection or an integrated connection; may be a mechanical connection or an electrical connection; and may be a direct connection or an indirect connection through an intermediate medium, or may be a communication between the interior of two elements. For those of ordinary skill in the art, the specific meaning of the terms mentioned above in the present disclosure should be construed according to specific circumstances.

The present disclosure is further described in detail below by particular embodiments and with reference to the accompanying drawings.

Figure 1:
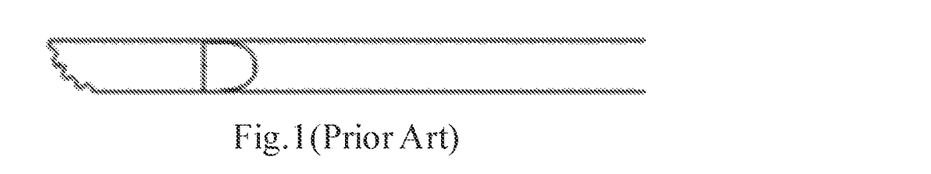
FIG. 1 is a schematic structural view of an ultrasonic scalpel bit in the prior art.
Figure 2:
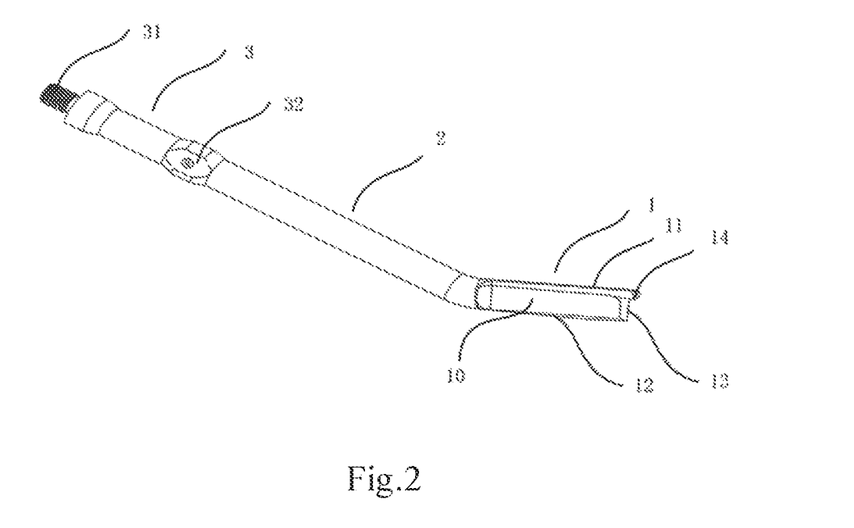
FIG. 2 is a schematic perspective view of an ultrasonic scalpel bit of a first embodiment of the present disclosure.
Figure 3:
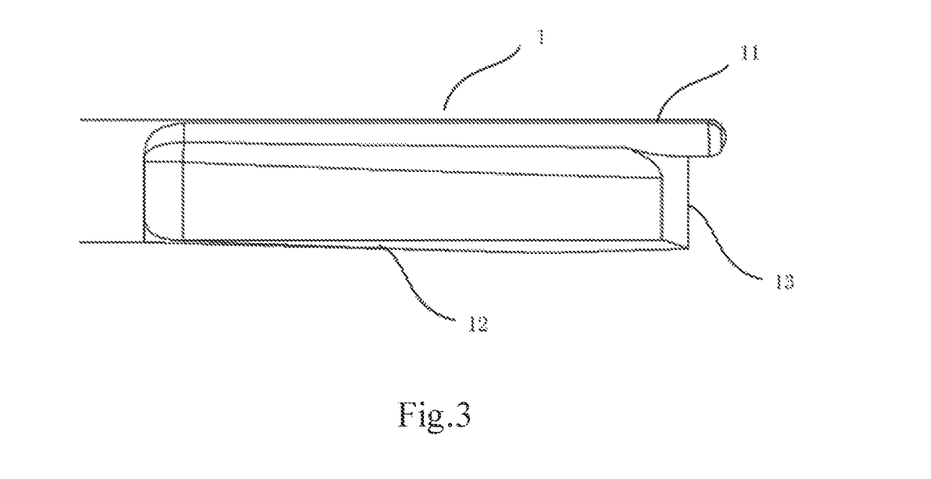
FIG. 3 is a front view of a bit tip of the ultrasonic scalpel bit of the first embodiment of the present disclosure.
Figure 4:
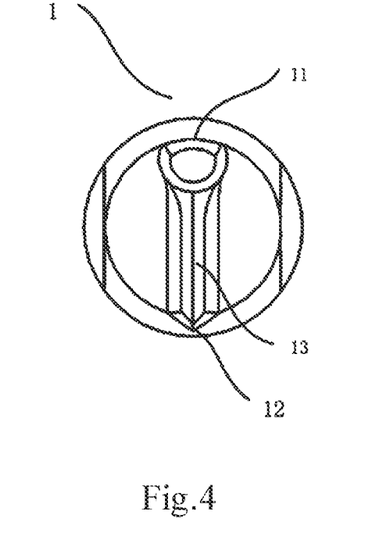
FIG. 4 is a right view of the bit tip of the ultrasonic scalpel bit of the first embodiment of the present disclosure.
Figure 5:
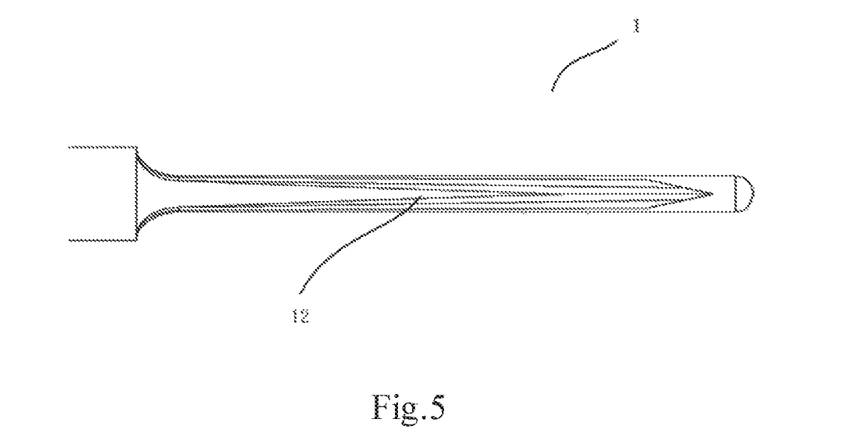
FIG. 5 is a bottom view of the bit tip of the ultrasonic scalpel bit of the first embodiment of the present disclosure.

FIGS. 2 to 5 show an ultrasonic scalpel bit of a first embodiment of the present disclosure. FIG. 2 is a schematic perspective view of the ultrasonic scalpel bit of the first embodiment of the present disclosure, FIG. 3 is a front view of a bit tip of the ultrasonic scalpel bit of the first embodiment, FIG. 4 is a right view of the bit tip of the ultrasonic scalpel bit, and FIG. 5 is a bottom view of the bit tip of the ultrasonic scalpel bit. As shown in FIGS. 2 to 5, the ultrasonic scalpel bit of the present disclosure comprises a bit tip 1, a bit bar 2, and a bit body 3. One end of the bit bar 2 is connected to the bit tip 1, and the other end of the bit bar 2 is connected to one end of the bit body 3. The other end of the bit body 3 is connected to a specific ultrasonic host via an ultrasonic transducer. In the ultrasonic scalpel bit of the first embodiment of the present disclosure, a main body of the bit tip 1 is flat (sheet-shaped) and is formed as a flat sheet structure 10. An upper and a lower face of the flat sheet structure 10 respectively form an upper bit ridge 11 and a lower bit ridge 12 of the bit tip 1. A protrusion 14 is formed at a front end of the upper bit ridge 11. The upper bit ridge 11 has a thickness greater than that of the flat sheet structure 10 and that of the lower bit ridge 12. The protrusion 14 is smooth and free of edges. That is to say, there is no sharp bit blade on the protrusion 14. The bit tip 1 is bent to one side at a portion that is connected to the bit bar 2, such that the bit tip 1 is at an angle to the bit bar 2. The protrusion 14 may be in the shape of a circle or an ellipse. The protrusion 14 transitions to a front end of the bit tip through a stepped portion, a circular arc-shaped portion or a bevel. The lower bit ridge 12 is edged to form a cutting blade. The front end of the bit tip 1 is provided with a front-end bit blade 13.

According to the ultrasonic scalpel bit of the first embodiment of the present disclosure, all the energy generated by the ultrasonic transducer can be concentrated to the front end portion of the bit, so that the front end portion of the bit of the tool has the highest energy output, achieving the strongest working effect. Meanwhile, since the ultrasonic scalpel bit of the first embodiment of the present disclosure has a head protection, it is possible to help a surgeon to bypass the spinal cord to perform a longitudinal cutting operation in a narrow space during a posterior osteotomy operation for vertebral body resection, so that it is possible to safely complete the operation without hurting the spinal cord, thereby significantly reducing the risk of the surgery.

In the ultrasonic scalpel bit of the first embodiment of the present disclosure, the bit tip 1 is bent to one side at a position where the bit tip is connected to the bit bar 2, such that the bit tip 1 is at an angle to the bit bar 2. The bit bar 2 may be of a hollow structure, and a liquid injection hole (not shown) may be provided in a portion of the bit bar 2 that is close to the bit tip 1 for directly injecting a rinsing liquid to the bit tip 1. It is also possible for the hollow part to extend up to the front end of the bit tip, and a liquid injection hole or groove (not shown) is provided in a side face of a cylindrical structure of the bit tip, or a side face of a flat-sheet-shaped cutting portion of the bit tip, or the foremost end of the bit tip. The ultrasonic scalpel bit is of a hollow structure, and the bit tip is provided with a liquid injection hole, which can ensure that the injected liquid flows out of the portion of the bit bar 2 that is close to the bit tip 1, and sufficient liquid can be injected. During surgery, the entire bit head and the contacted tissue are completely exposed to cleaning and cooling of the injected liquid in real time, so that excised tissues can be immediately discharged, the visual field at an incision is clear and clean, and the remaining tissues to be retained can be protected from being damaged. In this way, the risk of the surgery is further reduced, and the safety and success rate of surgery are improved.

Figure 6:
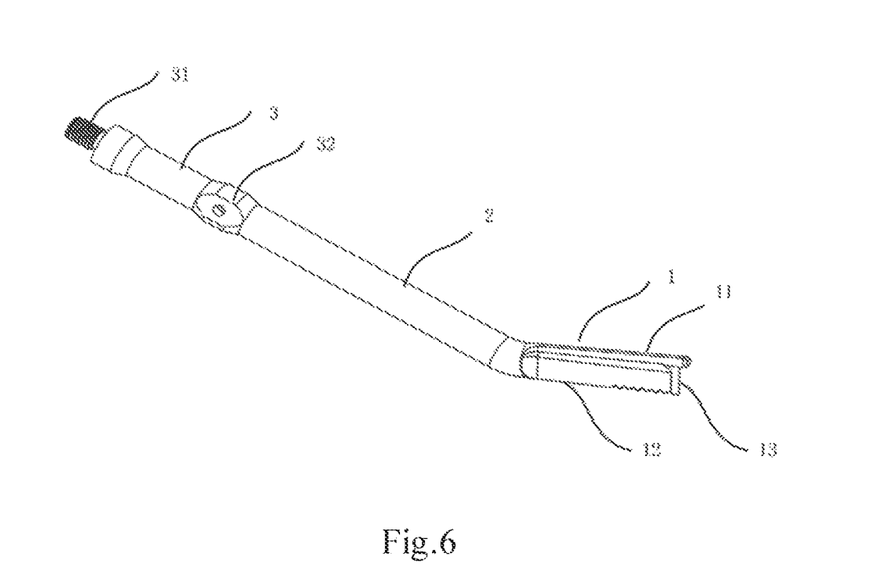
FIG. 6 is a schematic perspective view of an ultrasonic scalpel bit of a second embodiment of the present disclosure.
Figure 7:
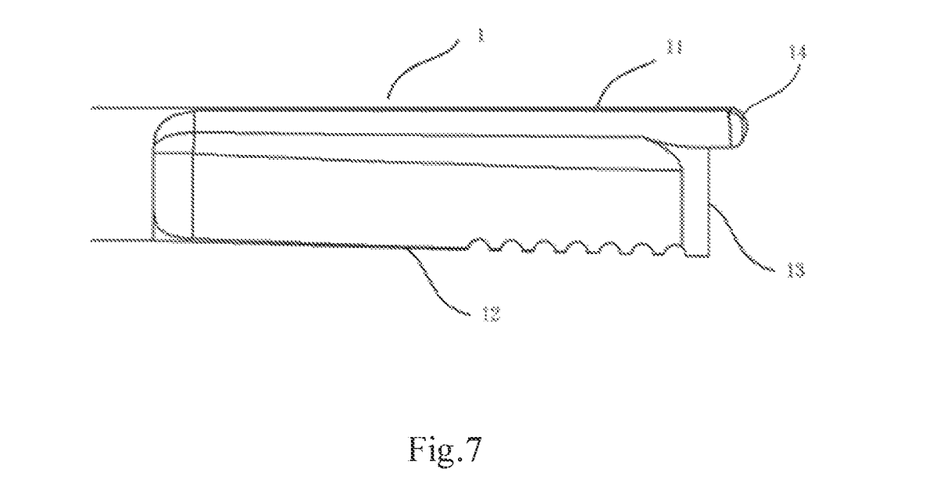
FIG. 7 is a front view of a bit tip of the ultrasonic scalpel bit of the second embodiment of the present disclosure.
Figure 8:
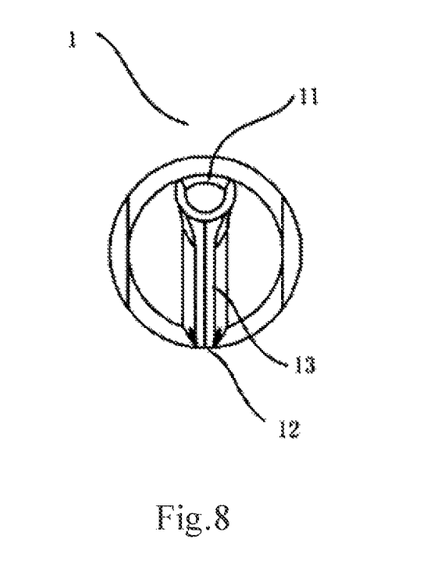
FIG. 8 is a right view of the bit tip of the ultrasonic scalpel bit of the second embodiment of the present disclosure.

FIGS. 6 to 8 show an ultrasonic scalpel bit of a second embodiment of the present disclosure. FIG. 6 is a schematic perspective view of the ultrasonic scalpel bit of the second embodiment of the present disclosure, FIG. 7 is a front view of a bit tip of the ultrasonic scalpel bit of the second embodiment, and FIG. 8 is a right view of the bit tip of the ultrasonic scalpel bit. As shown in FIGS. 6 to 8, the ultrasonic scalpel bit of the present disclosure comprises a bit tip 1, a bit bar 2, and a bit body 3. One end of the bit bar 2 is connected to the bit tip 1, and the other end of the bit bar 2 is connected to one end of the bit body 3. The other end of the bit body 3 is connected to a specific ultrasonic host via an ultrasonic transducer. Similarly to the first embodiment, in the ultrasonic scalpel bit of the second embodiment of the present disclosure, a main body of the bit tip 1 is flat (i.e. sheet-shaped) and is formed as a flat sheet structure 10. An upper and a lower face of the flat sheet structure 10 respectively form an upper bit ridge 11 and a lower bit ridge 12 of the bit tip 1. A protrusion 14 is formed at a front end of the upper bit ridge 11. The upper bit ridge 11 has a thickness greater than that of the flat sheet structure 10 and that of the lower bit ridge 12. The protrusion 14 is smooth and free of edges, and thus has no sharp bit blade. The protrusion 14 may be in the shape of a circle or an ellipse. The protrusion 14 transitions to a front end of the bit tip through a stepped portion, a circular arc-shaped portion or a bevel. The front end of the bit tip 1 is provided with a front-end bit blade 13. Compared with the first embodiment, the ultrasonic scalpel bit of the second embodiment of the present disclosure is different in that the lower bit ridge 12 is of a toothed structure. Each tooth 16 of the toothed structure may be in the shape of a triangle, a trapezoid or a circular arc. It is also possible to form the toothed structure on the basis that the lower bit ridge 12 has been edged, that is, to form a beveled, toothed structure.

According to the ultrasonic scalpel bit of the second embodiment of the present disclosure, the energy generated by the ultrasonic transducer can be more efficiently concentrated to the cutting portion, so that the working point of the bit has the highest energy output. In addition, the presence of the toothed structure can facilitate the positioning during surgery while improving the cutting efficiency. Meanwhile, since the ultrasonic scalpel bit of the second embodiment of the present disclosure also has the head protection, it is possible to help a surgeon to bypass the spinal cord for performing a longitudinal cutting operation in a narrow space during a posterior osteotomy operation for vertebral body resection, so that it is possible to safely complete the operation without hurting the spinal cord, thereby significantly reducing the risk of the surgery.

In the ultrasonic scalpel bit of the second embodiment of the present disclosure, the bit bar 2 may also be of a hollow structure, and a liquid injection hole (not shown) may be provided in a portion of the bit bar 2 that is close to the bit tip 1 for directly injecting rinsing liquid to the bit tip 1. One end of the bit bar 2 is connected to the bit tip 1, and the other end of the bit bar 2 is connected to the bit body 3. The bit bar 2 smoothly transitions to the bit body 3 through a bevel or a circular arc-shaped face. The ultrasonic scalpel bit is of a hollow structure, and the bit tip is provided with a liquid injection hole, which can ensure that the injected liquid flows out of the portion of the bit bar 2 that is close to the bit tip 1, and sufficient liquid can be injected. During surgery, the entire bit head and the contacted tissue can be completely exposed to cleaning and cooling of the injected liquid in real time, so that the risk of the surgery is further reduced, and the safety and success rate of surgery are improved.

Figure 9:
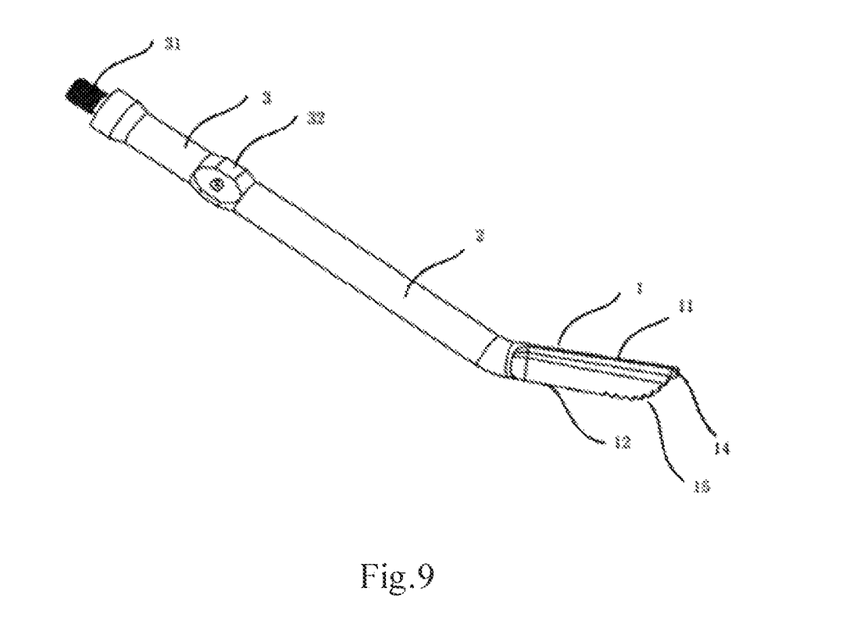
FIG. 9 is a schematic perspective view of an ultrasonic scalpel bit of a third embodiment of the present disclosure.
Figure 10:
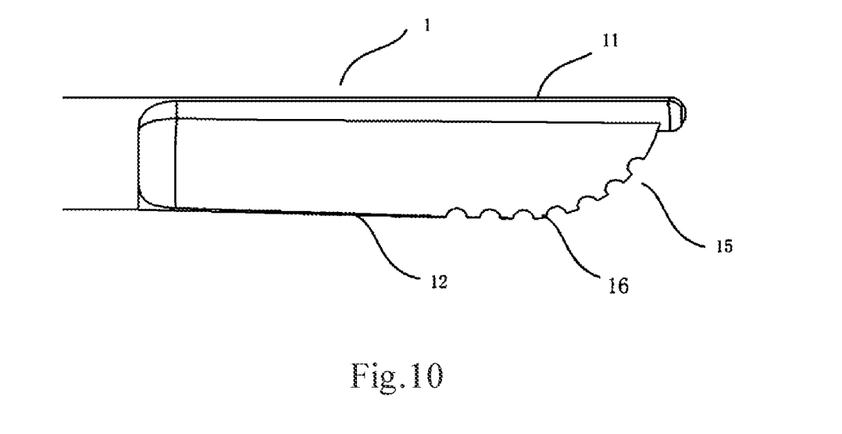
FIG. 10 is a front view of a bit tip of the ultrasonic scalpel bit of the third embodiment of the present disclosure.
Figure 11:
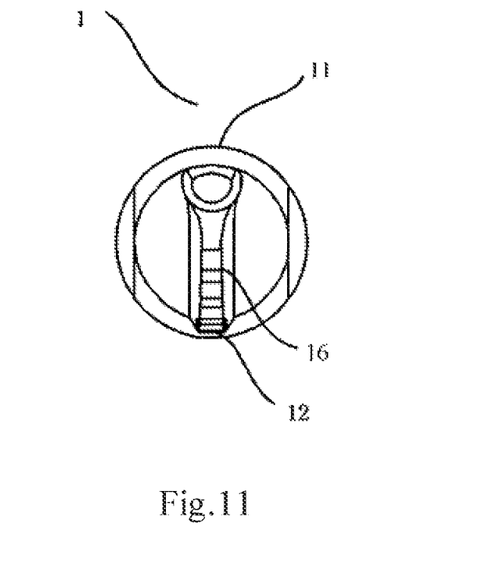
FIG. 11 is a right view of the bit tip of the ultrasonic scalpel bit of the third embodiment of the present disclosure.

FIGS. 9 to 11 show an ultrasonic scalpel bit of a third embodiment of the present disclosure. FIG. 9 is a schematic perspective view of the ultrasonic scalpel bit of the third embodiment of the present disclosure, FIG. 10 is a front view of a bit tip of the ultrasonic scalpel bit of the third embodiment, and FIG. 11 is a right view of the bit tip of the ultrasonic scalpel bit. As shown in FIGS. 9 to 11, the ultrasonic scalpel bit of the present disclosure comprises a bit tip 1, a bit bar 2, and a bit body 3. One end of the bit bar 2 is connected to the bit tip 1, and the other end of the bit bar 2 is connected to the bit body 3. The bit body 3 is connected to a specific ultrasonic host via an ultrasonic transducer. Similarly to the first and second embodiments, in the ultrasonic scalpel bit of the third embodiment of the present disclosure, a main body of the bit tip 1 is flat (i.e. sheet-shaped) and is formed as a flat sheet structure 10. An upper and a lower planar face of the flat sheet structure 10 respectively form an upper bit ridge 11 and a lower bit ridge 12 of the bit tip 1. A protrusion 14 is formed at a front end of the upper bit ridge 11. The upper bit ridge 11 has a thickness greater than that of the flat sheet structure 10 and that of the lower bit ridge 12. The protrusion 14 is smooth and free of edges. The protrusion 14 may be in the shape of a circle or an ellipse. The protrusion 14 transitions to a front end of the bit tip through a stepped portion, a circular arc-shaped portion or a bevel. The front end of the bit tip 1 is provided with a front-end bit blade 13. Compared with the first and second embodiments, the ultrasonic scalpel bit of the third embodiment of the present disclosure is different in that the upper bit ridge 11 transitions to the lower bit ridge 12 through a circular arc-shaped portion 15 at a front end portion of the bit tip 1. The circular arc-shaped portion is provided with teeth 16, forming a toothed structure. That is to say, in the third embodiment of the present disclosure, the lower bit ridge 12 of the bit tip 1 smoothly transitions to the front-end bit blade 13 of the bit tip through the circular arc-shaped portion 15 instead of forming a right angle. Similarly, each tooth 16 of the toothed structure may be in the shape of a triangle, a trapezoid or a circular arc. It is also possible to form the toothed structure on the basis that the circular arc-shaped portion has been edged, that is, to form a beveled, toothed structure.

According to the ultrasonic scalpel bit of the third embodiment of the present disclosure, the energy generated by the ultrasonic transducer can also be more efficiently concentrated to the cutting portion, so that the working point of the bit has the highest energy output. In addition, the presence of the circular arc-shaped toothed structure can facilitate the positioning during surgery while improving the cutting efficiency, and it is possible to apply the ultrasonic scalpel bit to more complicated surgical operations. Meanwhile, since the ultrasonic scalpel bit of the third embodiment of the present disclosure also has the head protection, it is possible to help a surgeon to bypass the spinal cord for performing a longitudinal cutting operation in a narrow space during a posterior osteotomy operation for vertebral body resection, so that it is possible to safely complete the operation without hurting the spinal cord, thereby significantly reducing the risk of the surgery.

Similarly, in the ultrasonic scalpel bit of the third embodiment of the present disclosure, the bit bar 2 may also be of a hollow structure, and a liquid injection hole (not shown) may be provided in a portion of the bit bar 2 that is close to the bit tip 1 for directly injecting rinsing liquid to the bit tip 1, so that sufficient liquid can be injected. In this way, during surgery, the entire bit head and the contacted tissue can be completely exposed to cleaning and cooling of the injected liquid in real time, so that the risk of the surgery is further reduced, and the safety and success rate of surgery are improved.

In addition, in the ultrasonic scalpel bit of the first to third embodiments, one end of the bit bar 2 is connected to the bit tip 1, and the other end of the bit bar 2 is connected to one end of the bit body 3. The bit bar 2 may smoothly transition to the bit body 3 through a bevel or a circular arc-shaped face. The other end of the bit body 3 is provided with connection threads 31. The connection threads 31 may be either internal or external. During a surgical operation, the connection threads 31 of the tail portion of the bit body 3 are connected to a specific ultrasonic transducer and are tightened using a corresponding wrench, and the ultrasonic transducer is then connected to a specific ultrasonic host, so that the ultrasonic scalpel bit is ready for operation.

Figure 12:
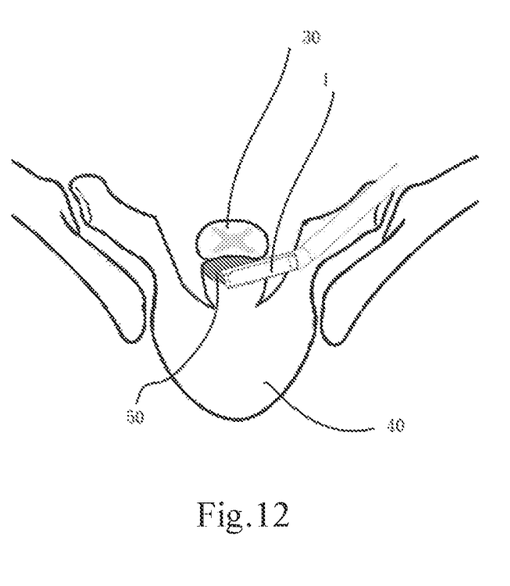
FIG. 12 is a schematic view showing an operation in the use of the ultrasonic scalpel bit of the present disclosure for surgery.

FIG. 12 is a schematic view showing the use of the ultrasonic scalpel bit of the first to third embodiments of the present disclosure for spinal surgery. As shown in FIG. 12, during surgery, the bit tip 1 of the ultrasonic scalpel bit of the present disclosure is interposed between a spinal cord 30 and a vertebra 40, to remove a lesion 50 compressing the spinal cord 30. Due to the relatively large thicknesses of the upper bit ridge 11 and the protrusion 14 of the bit tip 1, the spinal cord 30 can be protected from injury during surgery, so that the success rate of the surgery is improved, and the risk of the surgery is reduced.

The above various embodiments are merely used for illustrating rather than limiting the technical solutions of the present disclosure. Although the present disclosure has been described in detail with reference to the above various embodiments, those of ordinary skill in the art should understood that the technical solutions specified in the above various embodiments can still be modified, or some or all of the technical features therein can be equivalently substituted; and such modifications or substitutions do not make the essence of the corresponding technical solutions depart from the scope of the technical solutions of the various embodiments of the present disclosure.

The invention claimed is:

1. An ultrasonic scalpel bit, comprising a bit tip, a bit bar, and a bit body, one end of the bit bar being connected to the bit tip, and another end of the bit bar being connected to one end of the bit body, wherein:
   a main body of the bit tip is of a flat sheet structure, an upper and a lower face of which respectively form an upper bit ridge and a lower bit ridge of the bit tip;
   a protrusion is formed at a front end of the upper bit ridge;
   the upper bit ridge has a thickness greater than that of the flat sheet structure and that of the lower bit ridge;
   the protrusion is smooth and free of edges;
   wherein a front end of the bit tip is provided with a front-end bit blade;
   the protrusion extends beyond the front-end bit blade in an extending direction of the upper bit ridge;
   the front-end bit blade linearly extends perpendicular to the extending direction of the upper bit ridge and perpendicular to an extending direction of the lower bit ridge; and
   the lower bit ridge includes a cutting blade at a right angle with the front-end bit blade or a toothed structure.

2. The ultrasonic scalpel bit according to claim 1, wherein the bit tip is bent to one side at a portion of the bit tip that is connected to the bit bar, such that the bit tip is at an angle to the bit bar.

3. The ultrasonic scalpel bit according to claim 1, wherein the protrusion is shaped in a shape of a circle or an ellipse.

4. The ultrasonic scalpel bit according to claim 1, wherein the bit bar is of a hollow structure, the hollow structure extending up to the front end of the bit tip, and
   a liquid injection hole is provided in a side face of a cylindrical structure of the bit tip, a side face of a flat-sheet-shaped cutting portion of the bit tip, or a foremost end of the bit tip.

5. The ultrasonic scalpel bit according to claim 1, wherein the bit bar is connected to the bit tip and the one end of the bit body respectively through a bevel or a circular arc-shaped face with a smooth transition.

6. The ultrasonic scalpel bit according to claim 1, wherein another end of the bit body is connected to a specific ultrasonic host via an ultrasonic transducer, and the another end of the bit body is provided with connection threads, which are internal or external connection threads.

7. An ultrasonic scalpel bit, comprising a bit tip, a bit bar, and a bit body, one end of the bit bar being connected to the bit tip, and another end of the bit bar being connected to one end of the bit body, wherein:
   a main body of the bit tip is of a flat sheet structure, an upper and a lower face of which respectively form an upper bit ridge and a lower bit ridge of the bit tip;
   a protrusion is formed at a front end of the upper bit ridge;
   the upper bit ridge has a thickness greater than that of the flat sheet structure and that of the lower bit ridge;
   the protrusion is smooth and free of edges;
   wherein a front end of the bit tip is provided with a front-end bit blade;
   the protrusion extends beyond the front-end bit blade in an extending direction of the upper bit ridge;
   the front-end bit blade linearly extends perpendicular to the extending direction of the upper bit ridge and perpendicular to an extending direction of the lower bit ridge, wherein an end of the lower bit ridge of the bit tip forms a right angle with an end of the front-end bit blade; and
   the bit bar is of a hollow structure, the upper bit ridge is of a cylindrical structure, the hollow structure extending up to the front end of the bit tip, and a liquid injection hole is provided in a side face of the cylindrical structure of the bit tip.

8. The ultrasonic scalpel bit according to claim 7, wherein the lower bit ridge includes a cutting blade or a toothed structure.

* * * * *